United States Patent [19]

Goode et al.

[11] Patent Number: 4,988,347
[45] Date of Patent: Jan. 29, 1991

[54] METHOD AND APPARATUS FOR SEPARATING A COILED STRUCTURE FROM BIOLOGICAL TISSUE

[75] Inventors: Louis Goode, Evans City; Frederick J. Shipko, Spring Church, both of Pa.

[73] Assignee: Cook Pacemaker Corporation, Leechburg, Pa.

[21] Appl. No.: 269,771

[22] Filed: Nov. 9, 1988

[51] Int. Cl.$^5$ .............................................. A61B 17/00
[52] U.S. Cl. ......................................... 606/1; 128/785
[58] Field of Search ............... 128/783, 784, 785, 786, 128/419 P, 642, 328 V; 606/99

[56] References Cited

U.S. PATENT DOCUMENTS

| | | | |
|---|---|---|---|
| 3,243,755 | 3/1966 | Johnston | 439/841 |
| 3,516,412 | 6/1970 | Ackerman | 128/419 P |
| 3,841,308 | 10/1974 | Tate | 128/772 |
| 4,471,777 | 9/1984 | McCorkle, Jr. | 128/785 |
| 4,541,681 | 9/1985 | Dorman et al. | 339/100 |
| 4,574,800 | 3/1986 | Peers-Trevarton | 128/785 |
| 4,576,162 | 3/1986 | McCorkle | 128/785 |
| 4,582,056 | 4/1986 | McCorkle | 128/303 R |

FOREIGN PATENT DOCUMENTS 2558376 7/1985 France ................................ 128/785

OTHER PUBLICATIONS

Meibom, "A New Method for Transvenous Lead Explanation", 3rd European Symposium on Cardiac Pacing, Torremolinos, Malaga, Spain, PACE, vol. 8, May-June, 1985, Part II, Abstract 215, p.A-54.

Meibom et al., "A New Method for Removal of Embedded Endocardial Electrodes", First Asian-Pacific Symposium, PACE, vol. 3, May-Jun., 1980, Abstract No. 77, p. 380.

"Dotter Intravascular Retriever Set and Components", Cook ® Diagnostic and Interventional Products for Radiology, Cardiology and Surgery, Intravascular Retrieval, 1986, p. 3.

"Wilson-Cook Grasping Forceps", Wilson-Cook Medical, Inc., Products for Gastroenterology, Endoscopy and Surgery, 1986-1987 Catalog, p. 41.

"Loop Retrievers", Cook Urological ® Urological Surgical Products, Stone Extractors and Retrievers, 1986, p. 9.

"Boren-McKinney Retriever Set", Cook Urological ® Urological Surgical Products, Stone Extractors and Retrievers, 1986, p. 9.

"Curry Intravascular Retriever Sets and Components", Cook ® Diagnostic and Interventional Products for Radiology, Cardiology and Surgery, Intravascular Retrieval, 1986, p. 2.

"Grasping Forceps", Cook Urological ® Urological Surgical Products, Stone Extractors and Retrievers, 1986, p. 8.

Primary Examiner—Kyle L. Howell
Assistant Examiner—Kennedy J. Schaetzle
Attorney, Agent, or Firm—Richard J. Godlewski

[57] ABSTRACT

Heart lead removal apparatus is disclosed for removing a heart lead from the wall of a heart through a blood vessel leading to the heart. The apparatus comprises a flexible stylet wire with an expandable wire coil attached to the distal end for engaging the coiled structure of the heart lead. The stylet wire is inserted in the longitudinal passageway of the coiled structure to the distal end of the heart lead where the tip is typically secured to the heart wall with a number of tines formed from the insulating material surrounding the coiled structure. When inserted, the stylet wire is rotated in a direction to unwind and expand the wire coil and engage the heart lead coiled structure, thereby securing the stylet wire to the heart lead. A separator tube is inserted over the proximal end of the stylet wire and the heart lead and moved along the entire length of the heart lead to first separate the restricted heart lead from the blood vessel leading to the heart cavity. When fully inserted, the separator tube is positioned against the heart cavity wall, and the stylet wire is pulled while the separator tube is rotated back and forth to separate the heart lead tip from the heart wall. The separator tube, stylet wire, and heart lead are then removed from the heart cavity and blood vessel without causing any significant injury to the heart cavity wall.

24 Claims, 2 Drawing Sheets

METHOD AND APPARATUS FOR SEPARATING A COILED STRUCTURE FROM BIOLOGICAL TISSUE

TECHNICAL FIELD

This invention relates to coiled structures, such as an electrical, heart pacemaker lead, and particularly to method and apparatus for separating a coiled structure from biological tissue after the movement of the structure has become restricted in the tissue.

BACKGROUND OF THE INVENTION

A heart pacemaker is generally implanted subcutaneously in the chest wall along with a lead for conducting electrical signals, such as stimulating pulses, between the pacemaker and the heart. The lead is surgically implanted through a vein leading to a cavity of the heart. A typical heart lead includes one or more spirally coiled wires having a hollow inner passageway that extends the entire length of the coiled wires. The coiled wires are surrounded by a flexible tube or coating comprising, for example, silicone or polyurethane for insulating the wires from body fluids as well as each other. However, one problem is that, over time, fibrotic tissue commonly encapsulates the heart lead especially in areas where there is low velocity blood flow. When small diameter veins through which the lead passes become completely occluded with fibrotic tissue, separating the lead from the vein is difficult and causes severe damage to or destruction of the vein. Furthermore, the separation is usually not possible without restricting or containing the movement of the heart lead.

In most cases, the useful life of a heart lead lasts for many years. However, should the heart lead become inoperative due to corrosion or other effects of body fluids or should another heart lead be desired, the existing heart lead is typically left in place and a new heart lead is implanted through another vein. One problem with leaving an implanted heart lead in place, particularly in the heart, is that the lead partially restricts the operation of the various heart valves through which the lead passes. If several leads passing through a heart valve are left in place, the operation of the heart valve and the efficacy of the heart is significantly impaired.

Another problem associated with leaving heart leads in place, particularly in blood vessels, is that an infection may develop around the lead, thereby requiring surgical removal. Surgical removal of the lead from the heart involves open heart surgery which is complicated, risky, and costly.

One method for transvenous removal of a heart lead involves a prior art heart lead removal tool that utilizes a hollow, rigid tube and a beveled rod tip for engaging and deforming the coiled structure of the heart lead. However, when the heart lead cannot be removed because of some complication, a serious problem is that the tip of the tool is locked in place and cannot be removed from the heart lead. As a result, the tool and heart lead must be surgically removed. Furthermore, the rigid tube of the tool can easily puncture a blood vessel or a heart cavity wall.

Another method is to transvenously extract the heart lead manually without the aid of a tool. Such method is possible only when the lead has not ben encapsulated in a blood vessel. Even then, this method has a number of problems. First, when the polyurethane or silicone insulation covering is damaged, the lead covering can sever and cause the coiled structure of the lead to unwind and to damage the heart and blood vessels. Secondly, both the lead coil and covering can sever in the heart or a blood vessel and thus require surgical removal. Thirdly, most heart leads typically include tines or a conically shaped tip for securing the distal end of the heart lead to a heart cavity wall. After fibrotic tissue has encapsulated the tines or conically shaped tip, manual removal of the heart lead tip from the heart cavity wall may cause an inward extension or inversion of the wall, or even worse, permanent damage to the heart such as tearing a hole in the heart cavity wall.

SUMMARY OF THE INVENTION

The foregoing problems are solved and a technical advance is achieved with illustrative apparatus for separating a coiled structure from biological tissue such as an implanted electrical pacemaker lead encapsulated in a blood vessel leading to the heart. The illustrative heart lead removal apparatus comprises a flexible stylet wire insertable along the length of a hollow longitudinal passageway formed by the coiled structure of the heart lead for limiting the movement of the lead. A departure in the art is that the stylet wire is flexible and has expandable means such as a wire coil wrapped about the distal end for securing the stylet wire to the coiled structure of the heart lead. In the illustrative embodiment, a looped handle formed at the proximal end of the stylet wire rotates the stylet wire in a direction opposite to the direction that the coiled structure is wound to engage the wire coil on the stylet wire with the coiled structure. When the wire coil and coiled structure are engaged, the stylet wire is, as a result, firmly secured to the heart lead. This advantageously limits the movement of the heart lead and prevents the coiled structure from stretching, unraveling, or breaking during subsequent separation and removal from the blood vessel and heart cavity wall.

When the stylet wire is secured to the distal end of the heart lead, separator means such as a length of tube is inserted over the heart lead with the stylet wire secured thereto. The tube is made preferably from a material, such as a Teflon material, for moving easily over the heart lead and through the blood vessel. The distal end of the tube is beveled and has an edge for separating the heart lead from the blood vessel wall as the tube is moved along a length of the heart lead. The secured stylet wire advantageously limits movement of the heart lead to facilitate separation and also minimizes damage to the blood vessel as the tube is passed along a length of the heart lead separating the heart lead from the blood vessel wall.

After passing through the blood vessel, the tube is moved to the distal end of the heart lead next to the heart cavity wall for separating the tip of the lead from the heart tissue without causing injury thereto. The tube is held in place next to the heart cavity wall or pushed just slightly, while the stylet wire is pulled to engage the tip of the heart lead against the beveled distal end of the tube. A silver solder bead at the end of the stylet wire prevents the stylet wire from being pulled through the wire coil. The tube is then rotated back and forth to cause the tines at the tip of the heart lead to dislodge and separate from the trabeculae and fibrotic tissue that secure the lead to the heart cavity wall. As a result, the tip of the heart lead is advantageously separated from the heart wall without causing injury to the heart tissue.

Another advantage of this lead removal apparatus is when the lead cannot be removed because of some complication. In such case, the separator tube is removed from the blood vessel, and the stylet wire is rotated to unsecure and unscrew the wire coil and the stylet wire from the coiled structure of the heart lead. This advantageously permits the removal of the stylet wire from the coiled structure without having to perform open heart surgery. This represents a significant advantage over the prior art device in which the beveled rod and an actuating wire cannot be removed from the heart lead after the distal end has engaged and deformed the coiled structure. In such instance, open heart surgery is then required to remove the lead.

The tolerance between the inside dimension of the coiled structure and the combined outside dimension of the wire coil and stylet wire is maintained at a predetermined tolerance to permit the easy engagement of the wire coil with the coiled structure.

The invention also includes the method of separating the coiled structure from the tissue by inserting the distal end of the stylet wire with the wire coil attached thereto into the longitudinal passageway of the coiled structure. A rotation of the stylet wire is advantageously used to free the stylet wire and wire coil if there is a tendency for the stylet wire to prematurely engage the coiled structure of the heart lead. After the stylet wire is fully inserted, the stylet is rotated a number of times usually in a counterclockwise direction to engage the wire coil with the coiled structure. As a result, the stylet wire is secured to the coiled structure. After the stylet wire is secured to the heart lead, a tube is inserted over the heart lead with the stylet wire inserted therein. As the tube is pushed along the heart lead, the stylet wire limits the movement of the heart lead to permit the separation of the heart lead from an occluded blood vessel. When fully inserted to the heart lead tip, the tube is held in place or pushed slightly, and the stylet wire is pulled to engage the tip of the heart lead with the beveled distal end of the tube. The separator tube is then rotated back and forth to dislodge the tines and separate the tip of the lead from the heart cavity wall without causing any trauma thereto.

Since the coiled structure of the heart lead is commonly wrapped in a clockwise direction, the stylet wire coil is wrapped around the stylet wire in a counterclockwise direction opposing the direction of the coiled structure. This permits the easy engagement and disengagement of the stylet wire with the heart lead when the stylet wire is rotated in either a counterclockwise or clockwise direction.

BRIEF DESCRIPTION OF THE DRAWING

FIG. 3 illustrates sections of the apparatus of the present invention for separating a length of a heart lead restricted in a blood vessel and for separating the tip of the heart lead from a heart cavity wall; and FIG. 4 illustrates the leading edge of the separator tube of the apparatus of FIG. 3 for separating the heart lead from a blood vessel as partially shown in FIG. 1.

DETAILED DESCRIPTION

Figure 1:
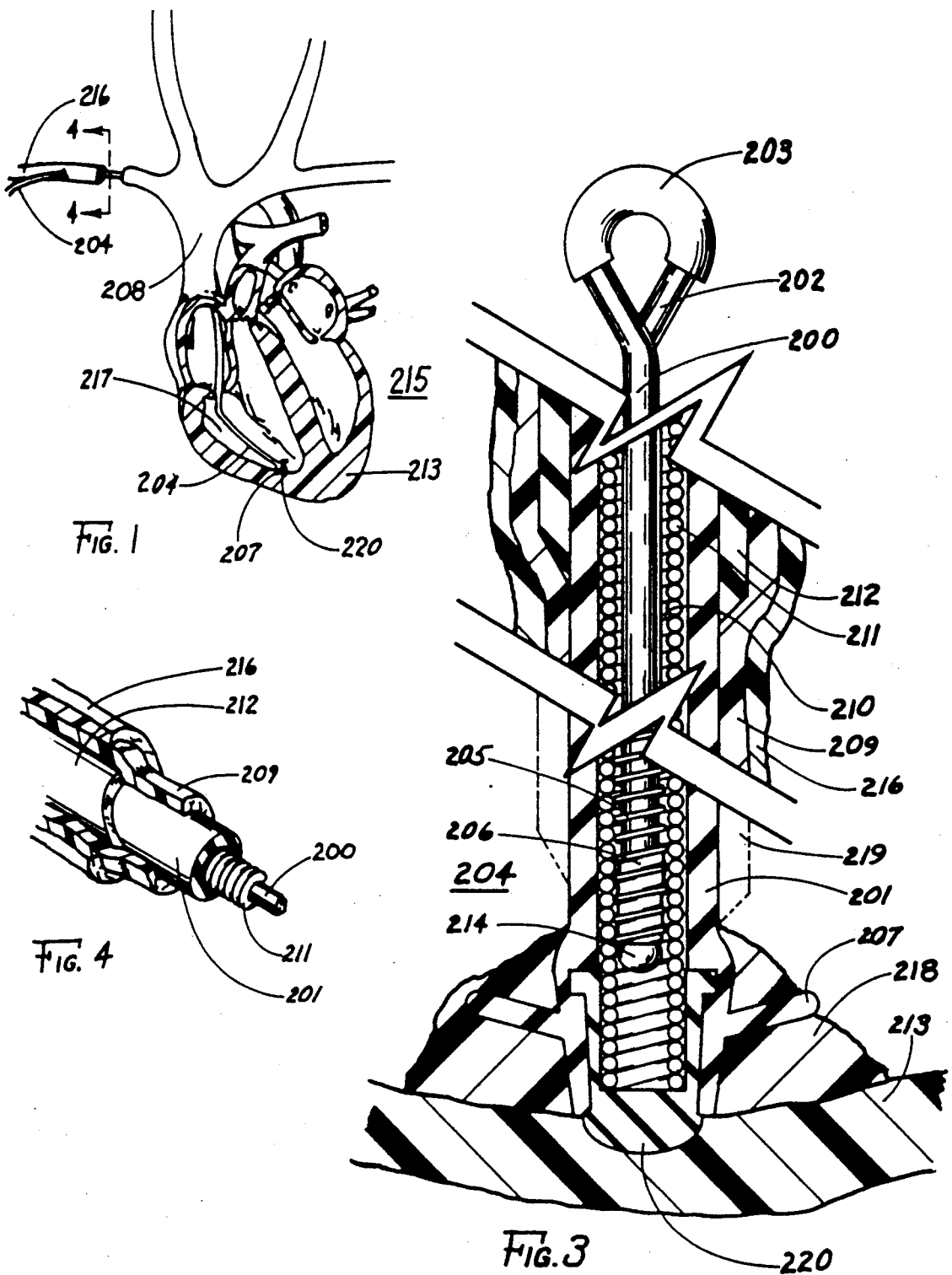
FIG. 1 depicts a partial cross-sectional view of a heart having an electrical pacemaker lead implanted therein.

Depicted in FIG. 1 is a partial cross-sectional view of heart 215 connected to a plurality of arteries and veins such as the right subclavian vein 216 through which an electrical heart pacemaker lead 204 has been implanted. The lead passes through the superior vena cava 208 and into the right ventricle 217 of the heart. The distal end of the lead includes an electrode 220 for electrically stimulating the heart and is secured to the apex of the right ventricle with a plurality of tines 207, which in time become securely attached to the ventricle wall by endothelial tissue forming around the heart lead tip. Some ventricles are relatively smooth on the inside, but most have trabeculae amongst which the tines are secured into position.

Figure 2:
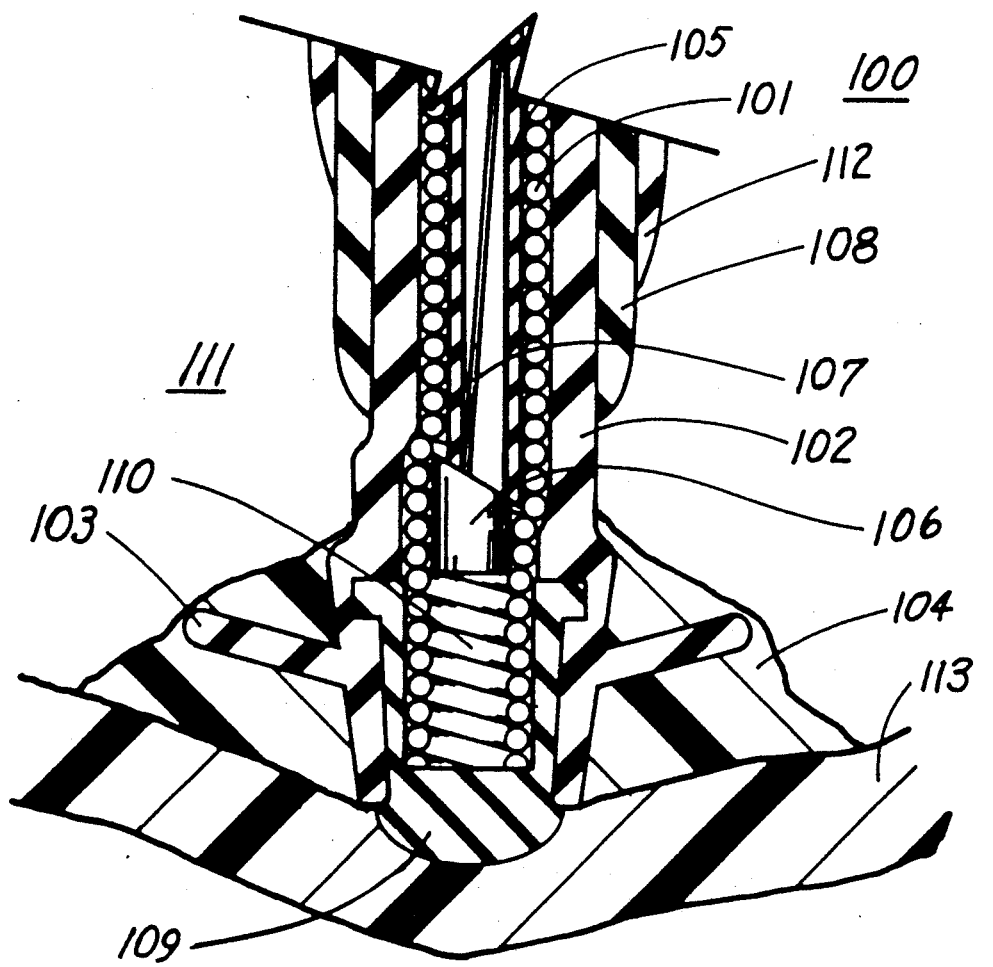
FIG. 2 depicts a partial cross-sectional view of a prior art tool inserted in the passageway of a heart lead for removing the lead.

Depicted in FIG. 2 is a partial cross-sectional view of a prior art tool 100 for removing a heart lead 111 which has been secured to a heart cavity wall 113 via trabeculae and/or fibrotic tissue 104. The lead includes an electrical coiled structure 101 and insulating material 102 that is formed essentially into a tube for covering the outer surface of the coiled structure and for preventing fluids from entering the coiled structure. At the distal end of the heart lead are tines 103, that are formed from the insulating material, for securing the heart lead tip including electrode 109 to the heart cavity wall. Tool 100 includes a hollow rigid tube 105 and beveled rod 106 for inserting in the longitudinal passageway 110 of the heart lead coiled structure. In the passageway of hollow tube 105 is an actuating wire 107 connected to beveled rod 106. The trailing edge of the beveled rod and the leading edge of the hollow tube are inclined at an angle for moving the beveled rod across the distal end of the hollow tube when the actuating wire is pulled. When moved, the beveled rod engages and deforms the heart lead coiled structure as shown. The deformed coiled structure locks the hollow tube and beveled rod in place for limiting movement of the heart lead. However, once secured, beveled rod 106 may not be extracted from passageway 110 of the coiled structure since the deformed coiled structure prevents the beveled rod and actuating wire from traversing the passageway. The prior art tool also includes a hollow dilator 108 for sliding over the heart lead coil and separating the heart lead from the blood vessel. A hollow explanator 112 passes over the dilator and is rotated back and forth to explant the tip of the heart lead from the securing tissue and heart wall.

Depicted in FIG. 3 is a flexible stylet wire 200 of the present lead removal apparatus invention that is insertable in the longitudinal passageway 210 of a heart lead coiled structure 211 for limiting the movement of heart lead 204 including coiled structure 211. Heart lead 204 also includes insulating material 201, such as silicone or polyurethane, that surrounds the coiled structure and prevents fluids from making contact with the coiled structure. Attached to the distal end of the flexible stylet wire is an expandable wire coil 205 consisting of approximately 25 turns of wire with spacing between the turns. Five to seven wrap of the wire coil are attached to the distal end of the stylet wire using, for example, solder 206. The remaining wraps of the wire coil remain free for engaging the coiled structure when the proximal end of the stylet wire is rotated in a direction to unwind and expand the turns of the wire coil and engage the coiled structure of the heart lead. A bead 214 of high temperature silver solder is applied to the distal end of the stylet wire to prevent the distal end thereof from pulling through the wire coil during separation and removal of the heart lead. The proximal end of the stylet wire is formed into a loop 202 or fashioned for attachment to another control mechanism for rotating the stylet wire in either a clockwise or counterclockwise direction or for moving the wire in a longitudinal direction. The formed loop 202 is covered with a Teflon material tubing suitable material for facilitating the easy movement of the stylet wire. The looped end is also compressible for inserting through a separator tube 212.

The choice of the stylet wire and coil wire varies with the internal diameter of the coiled structure which varies from 0.016" to about 0.028" for most heart leads. The diameter of the stylet wire would then range from 0.009" to 0.015", with the coil wire ranging in diameter from 0.003" to 0.006". The use of stainless steel wire is preferable. The stylet wire should be hardened wire, but ductable wire may be used for the coil wire.

As shown in FIG. 3, stylet wire 200 is inserted into longitudinal passageway 210 of coiled structure 211. The diameter of the coil wire and stylet wire have been selected to form a combined overall diameter which approximates the diameter of the longitudinal passageway of the heart lead coiled structure within a predetermined tolerance such as one or two thousandths of an inch. Stylet wire 200 is then fed through the entire length of the passageway to the distal end of the heart lead coiled structure which is secured to the wall of heart cavity tissue 213. When fully inserted into the heart lead, the distal ends of the stylet wire and heart lead coiled structure should be in close proximity. It is not necessary, but probably more advantageous, that the stylet wire be attached to the distal end of the heart lead. For separating the heart lead from adjacent tissue, the stylet wire may be secured anywhere along the passageway of the heart lead coiled structure past the restricting tissue. To engage the heart lead coiled structure 211, looped end 202 of the stylet wire is operated in a circular direction to unwind and expand wire coil 205. As a result, the turns of the wire coil and coiled structure engage and intermesh, thereby firmly securing the stylet wire to the heart lead. This prevents any extension or stretching of the heart lead and also limits the movement of the lead when separator tube 212 is moved along the length of coiled structure 211 and insulating material 201 of the heart lead.

As previously suggested, the looped proximal end of the stylet wire can be compressed to permit separator tube 212 to be inserted thereover and over the insulating material of the heart lead. Separator tube 212 comprises a semi-rigid material, such as teflon, for sliding easily through the blood vessel and over the insulating material of the heart lead. In order to place the separator tube over the stylet, it is necessary that the stylet extend at least 12 inches beyond the person's body so that the looped end can be grasped to apply tension to the stylet. With the separator tube 10 to 12 inches long, the stylet is typically three feet long.

Depicted in FIG. 4 is fibrotic tissue 209 encapsulating heart lead 204 in blood vessel vein 216. When this occurs in small diameter veins where blood flow has been restricted or prevented, separation and removal of the lead from the tissue is difficult and often causes severe damage or destruction to the vein. Without tension on stylet wire 200, separation is usually not possible in these situations.

As shown, the distal end of the separator tube 212 is beveled and includes a cutting edge or edge having a number of teeth for separating heart lead insulating material 201 from encapsulating fibrotic tissue 209.

Returning the reader's attention to FIG. 3, separator tube 212 is pushed and rotated along the outer surface of the insulating material 201 of the heart lead to separate the lead from the blood vessel wall. After the separator tube has been moved along the entire length of the heart lead, it will abut next to the heart cavity wall as shown by phantom lines 219. The distal end of the heart lead is typically secured to the heart cavity wall by trabeculae or fibrotic tissue 218 that has encapsulated tines 207 positioned at the distal end of the lead. The separator tube 212 is positioned next to the heart cavity wall or pushed slightly while the stylet wire is tensioned in the opposite direction. The separator tube is then rotated back and forth to dislodge and separate tines 207 and the distal end of the heart lead from fibrotic tissue 218 and heart cavity wall 213. As a result, the heart lead has now been completely separated from the blood vessel and the heart cavity wall for subsequent removal. The separator tube, the stylet wire, and the heart lead are then removed from the heart cavity and surrounding blood vessel.

However, should the removal of the heart lead be prevented for whatever reason, the stylet wire is rotated in a clockwise direction to unsecure the stylet and wire coil from the heart lead coiled structure. The time for this operation is lessened by attaching a rotating mechanism such as an electrical screwdriver to the proximal end of the stylet wire.

Of course, it will be understood that the aforementioned lead removal apparatus or tool is merely illustrative of the application of the principles of this invention and that numerous other arrangements may be devised by those skilled in the art without departing from the spirit and scope of the invention. In particular, a number of other control mechanisms can be used to attach to the proximal end of the stylet wire for operating the stylet wire in either a clockwise or counterclockwise direction as well as moving the wire longitudinally. Furthermore, this apparatus may be utilized for removing electrical leads from body ducts and passages as well as body tissue that have encapsulated the lead and restricted its movement.

What is claimed is:

1. Apparatus for separating a length of a coiled structure having a longitudinal passageway therein from biological tissue, comprising:
    wire means having a distal end for inserting in said longitudinal passageway of said coiled structure;
    coil means attached about said distal end of said wire means for radially expanding and securing said wire means to said coiled structure; and
    tube means positionable about said wire means and said length of said coiled structure for separating said coiled structure from said biological tissue when said wire means is secured to said coiled structure.

2. The apparatus of claim 1 further comprising control means positionable about a proximal end of said wire means for rotating said radially expandable means to engage said coiled structure.

3. The apparatus of claim 1 wherein a distal end of said tube means has a cutting edge.

4. The apparatus of claim 1 wherein said radially expandable means includes turns of wire.

5. Method of separating a coiled structure from biological tissue, comprising the steps of:
inserting a wire in a longitudinal passageway of said coiled structure,
securing said wire to said coiled structure with a coil attached about a distal end of said wire, and
separating a length of said coiled structure restricted in said tissue with a tube positioned about and moved along said length of said coiled structure when said wire is secured to said coiled structure.

6. The method of claim 5 further comprising the steps of moving said tube to a distal end of said coiled structure adjacent other tissue, engaging said distal end of said coiled structure against said distal end of said tube 1 and separating said distal end of said coiled structure from said other tissue.

7. The method of claim 6 wherein the step of engaging said distal end of said coiled structure against said distal end of said tube includes pulling said wire secured to said distal end of said coiled structure.

8. The method of claim 7 further comprising the step of removing said coiled structure from said tissue when said distal end of said coiled structure is separated from said other tissue.

9. The method of claim 6 wherein the step of separating includes rotating said tube and dislodging said distal end of said coiled structure from said other tissue.

10. The method of claim 5 further comprising the steps of unsecuring said wire from said coiled structure when said coiled structure is inseparable from said tissue and removing said wire from said passageway.

11. Apparatus for separating a blood vessel and a length of an electrical lead restricted in said blood vessel, said lead having a proximal end and including a coiled structure wound in a first direction and having a longitudinal passageway therein, comprising:
limiting means for inserting into said longitudinal passageway of said electrical lead;
expandable means attached to said limiting means for securing said limiting means to said electrical lead at a predetermined distance away from said proximal end of said electrical lead; and
separator means positionable about said limiting means and said length of said electrical lead and movable therealong for separating said blood vessel and said electrical lead restricted in said blood vessel when said limiting means is secured to said electrical lead.

12. The apparatus of claim 11 wherein a distal end of said separator means includes an edge for separating said lead from said blood vessel as said separator means is moved along said length of said electrical lead.

13. The apparatus of claim 11 wherein said expandable means includes a wire coil positioned about said distal end of said limiting means and wound in a second direction opposing said first direction of said coiled structure of said heart lead.

14. Apparatus for removing a heart lead having a longitudinal passageway therein and a distal end secured to heart tissue, said passageway having a predetermined dimension, comprising:
a stylet wire having distal end means for inserting into said longitudinal passageway of said heart lead;
a wire coil attached to said distal end means of said stylet wire and including expandable means for securing said distal end means of said stylet wire to said distal end of said heart lead, said expandable means in a first state having an outside dimension within a predetermined tolerance of said predetermined dimension and in an expanded state engaging said heart lead when in said passageway; and
a tube including distal tube end means for separating said distal end of said heart lead secured to said heart tissue when said tube is positioned about said stylet wire and said distal end of said heart lead, and said stylet wire is secured to said distal end of said heart lead.

15. The apparatus of claim 14 wherein said expandable means comprises a plurality of turns of wire positioned about said distal end of said stylet wire.

16. The apparatus of claim 14 wherein said distal end tube means includes cutting edge means for separating said distal end of said heart lead from said heart tissue as said distal end tube means is engaged against said heart tissue when said stylet wire is secured to said distal end of said heart lead.

17. The apparatus of claim 14 wherein said tube comprises semi-rigid material means for sliding over said heart lead and through a blood vessel leading to said heart tissue.

18. The apparatus of claim 14 wherein said predetermined tolerance is less than two one thousandths of an inch.

19. Apparatus for separating a coiled structure from biological tissue, said structure having a longitudinal passageway therein and a proximal end, comprising:
flexible means insertable in said longitudinal passageway of said coiled structure for limiting movement of said coiled structure,
expandable means attached to said flexible means for securing said flexible means to said coiled structure at a position within said passageway away from said proximal end of said coiled structure, and
separator means positionable about said flexible means and said coiled structure for separating said coiled structure from said biological tissue when said flexible means is secured to said coiled structure.

20. The apparatus of claim 19 wherein said flexible means comprises a flexible stylet wire.

21. The apparatus of claim 19 wherein said expandable means comprises a wire coil.

22. The apparatus of claim 19 wherein said separator means comprises a hollow tube.

23. Apparatus for removing a coiled structure from biological tissue, said structure including a longitudinal passageway having a predetermined dimension therein, comprising:
a wire having distal end means for inserting in said longitudinal passageway of said coiled structure;
a coil attached about said distal end means of said wire and including expandable means for securing said wire to said coiled structure at a position within said passageway distal from said proximal end of said coiled structure, said expandable means in a first state having an outside dimension within a predetermined tolerance of said predetermined dimension and in an expanded state engaging said coiled structure when in said passageway; and
control means positioned about a proximal end of said wire for removing said coiled structure from said tissue when said wire is secured to said coiled structure.

24. The apparatus of claim 23 further comprising tube means positionable about said wire and said coiled structure for separating said coiled structure from said biological tissue when said wire is secured to said coiled structure.

* * * * *